(12) United States Patent
Hasumi et al.

(10) Patent No.: US 8,784,830 B2
(45) Date of Patent: Jul. 22, 2014

(54) ANTIGEN PEPTIDE AND USE THEREOF

(76) Inventors: Kenichiro Hasumi, Tokyo (JP); Mikio Kuraya, Tokyo (JP)

( * ) Notice: Subject to any disclaimer, the term of this patent is extended or adjusted under 35 U.S.C. 154(b) by 0 days.

(21) Appl. No.: 13/380,425

(22) PCT Filed: May 23, 2011

(86) PCT No.: PCT/JP2011/062305
§ 371 (c)(1),
(2), (4) Date: Dec. 22, 2011

(87) PCT Pub. No.: WO2011/149099
PCT Pub. Date: Dec. 1, 2011

(65) Prior Publication Data
US 2012/0301495 A1 Nov. 29, 2012

Related U.S. Application Data

(60) Provisional application No. 61/396,574, filed on May 27, 2010.

(51) Int. Cl.
| | |
|---|---|
| A61K 39/05 | (2006.01) |
| C07K 14/195 | (2006.01) |
| C12N 15/31 | (2006.01) |
| C12Q 1/68 | (2006.01) |
| C07K 16/12 | (2006.01) |
| A61P 31/04 | (2006.01) |
| A61P 17/10 | (2006.01) |
| C07K 7/08 | (2006.01) |
| C12N 15/63 | (2006.01) |

(52) U.S. Cl.
USPC ...... 424/190.1; 530/323; 530/327; 530/387.9

(58) Field of Classification Search
None
See application file for complete search history.

(56) References Cited

FOREIGN PATENT DOCUMENTS

| | | |
|---|---|---|
| CA | 2 407 352 A1 | 11/2001 |
| JP | 2004-520803 A | 7/2004 |
| WO | WO 2010039750 A2 * | 4/2010 |
| WO | WO 2010/065735 A2 | 6/2010 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Colman (Res. Immunology, Jan. 1994, vol. 145, pp. 33-36).*
Written Opinion of the International Searching Authority of PCT/JP2011/062305.
SubName:Full= Outer membrane . . . , XP002675395, retrieved from EBI accession No. UNIPROT: Unreviewed, Sep. 13, 2004, Database accession No. Q6A6X7.
SubName:Full= Conserved membrane . . . , XP002675396, retrieved from EBI accession No. UNIPROT: Unreviewed, Sep. 13, 2004, Database accession No. Q6A5A4.
European Search Report dated Jun. 4, 2012 for European Application No. 11786796.0.
Brüggemann, H. et al., "The Complete Genome Sequence of Propionibacterium Acnes, a Commensal of Human Skin"; *Science* 305, 671 (2004); pp. 671-673.
Nakatsuji, T. et al., "Vaccination Targeting a Surface Sialidase of *P. acnes:* Implication for New Treatment of Acne Vulgaris"; PLoS ONE; Feb. 2008; vol. 3; Issue 2; e1551; pp. 1-9.
Ramstad, S. et al., "The temperature dependence of porphyrin production in *Propionibacterium acnes* after incubation with 5-aminolevulinic acid (ALA) and its methyl ester (m-ALA)"; *Photochem. Photobiol. Sci.*, 2006, 5, pp. 66-72.
Lodes, M. et al., "Variable expression of immunoreactive surface proteins of *Propionibacterium acnes*"; *Microbiology* 2006; 152, pp. 3667-3681.
Kuraya, M. "Possibility of acne vaccine"; Medical Beauty Forum Autumn & Winter; Feb. 7, 2010; Forum 3.
International Search Report for PCT/JP2011/062305 mailed on Jun. 21, 2011.

* cited by examiner

*Primary Examiner* — Robert A Zeman
(74) *Attorney, Agent, or Firm* — Eckert Seamans Cherin & Mellott, LLC; Carol A. Marmo

(57) ABSTRACT

In order to provide an effective vaccine against infection with *Propionibacterium acnes*, the present invention provides a peptide which is a peptide consisting of a specific amino acid sequence or a peptide consisting of an amino acid sequence derived from the specific amino acid sequence by deletion, substitution, insertion, or addition of one or more amino acids, the peptide suppressing, by immune response, inflammation caused by infection with *Propionibacterium acnes*.

12 Claims, 8 Drawing Sheets

F I G. 4
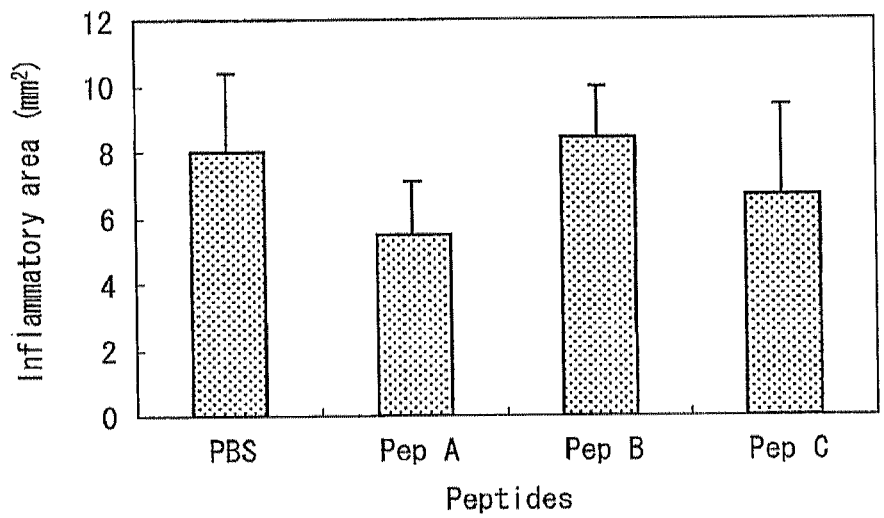
F I G. 5
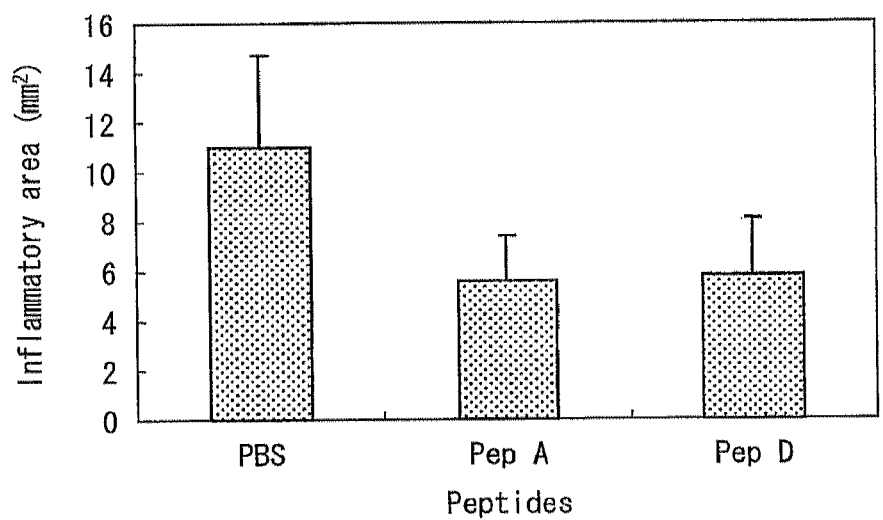

FIG. 6

| BACTERIAL STRAINS | No. | sequence | | | | |
|---|---|---|---|---|---|---|
| SEPARATED BACTERIAL STRAINS (SEQ NO.16) | 4 | | GTTTGATCCT | GGCTCAGGAC | GAACGCTGGC | GGCGTGCTTA ACACATGCAA |
| ATCC 6919 (SEQ NO. 8) | 1 | AGA | GTTTGATCCT | GGCTCAGGAC | GAACGCTGGC | GGCGTGCTTA ACACATGCAA |
| SEPARATED BACTERIAL STRAINS | 54 | GTCGAACGGA | AAGGCCCTGC | TTTTGTGGGG | TGCTCGAGTG | GCGAACGGGT |
| ATCC 6919 | 54 | GTCGAACGGA | AAGGCCCTGC | TTTTGTGGGG | TGCTCGAGTG | GCGAACGGGT |
| SEPARATED BACTERIAL STRAINS | 104 | GAGTAACACG | TGAGTAACCT | GCCCTTGACT | TTGGGATAAC | TTCAGGAAAC |
| ATCC 6919 | 104 | GAGTAACACG | TGAGTAACCT | GCCCTTGACT | TTGGGATAAC | TTCAGGAAAC |
| SEPARATED BACTERIAL STRAINS | 154 | TGGGGCTAAT | ACCGGATAGG | AGCTCCTGCT | GCATGGTGGG | GGTTGGAAAG |
| ATCC 6919 | 154 | TGGGGCTAAT | ACCGGATAGG | AGCTCCTGCT | GCATGGTGGG | GGTTGGAAAG |
| SEPARATED BACTERIAL STRAINS | 204 | TTTCGGCGGT | TGGGGATGGA | CTCGCGGCTT | ATCAGCTTGT | TGGTGGGGTA |
| ATCC 6919 | 204 | TTTCGGCGGT | TGGGGATGGA | CTCGCGGCTT | ATCAGCTTGT | TGGTGGGGTA |
| SEPARATED BACTERIAL STRAINS | 254 | GTGGCTTACC | AAGGCTTTGA | CGGGTAGCCG | GCCTGAGAGG | GTGACCGGCC |
| ATCC 6919 | 254 | GTGGCTTACC | AAGGCTTTGA | CGGGTAGCCG | GCCTGAGAGG | GTGACCGGCC |
| SEPARATED BACTERIAL STRAINS | 304 | ACATTGGGAC | TGAGATACGG | CCCAGACTCC | TACGGGAGGC | AGCAGTGGGG |
| ATCC 6919 | 304 | ACATTGGGAC | TGAGATACGG | CCCAGACTCC | TACGGGAGGC | AGCAGTGGGG |
| SEPARATED BACTERIAL STRAINS | 354 | AATATTGCAC | AATGGGCGGA | AGCCTGATGC | AGCAACGCCG | CGTGCGGGAT |
| ATCC 6919 | 354 | AATATTGCAC | AATGGGCGGA | AGCCTGATGC | AGCAACGCCG | CGTGCGGGAT |
| SEPARATED BACTERIAL STRAINS | 404 | GACGGCCTTC | GGGTTGTAAA | CCGCTTTCGC | CTGTGACGAA | GCGTGAGTGA |
| ATCC 6919 | 404 | GACGGCCTTC | GGGTTGTAAA | CCGCTTTCGC | CTGTGACGAA | GCGTGAGTGA |
| SEPARATED BACTERIAL STRAINS | 454 | CGGTAATGGG | TAAAGAAGCA | CCGGCTAACT | ACGTGCCAGC | AGCCGCGGTG |
| ATCC 6919 | 454 | CGGTAATGGG | TAAAGAAGCA | CCGGCTAACT | ACGTGCCAGC | AGCCGCGGTG |
| SEPARATED BACTERIAL STRAINS | 504 | ATAC | | | | |
| ATCC 6919 | 504 | ATAC GTAG | | | | |

ANTIGEN PEPTIDE AND USE THEREOF

CROSS-REFERENCES TO RELATED APPLICATIONS

The present application is the 35 U.S.C. §371 national stage of PCT international application PCT/JP2011/062305, filed May 23, 2011, which claims benefit under 35 U.S.C. §119(e) on U.S. Provisional Application Ser. No. 61/396,574 filed on May 27, 2010, the entire contents of all of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Dec. 15, 2011, is named 86517904.txt and is 4,837 bytes in size.

TECHNICAL FIELD

The present invention relates to an antigen peptide against *Propionibacterium acnes* and use of the antigen peptide.

BACKGROUND ART

Acne is an inflammatory disease that often appears on portions from neck to face of a human body mainly during puberty and also in adulthood. Due to a position where inflammation occurs, the appearance of acne has a great psychological influence on a person.

So far, various therapeutic agents for acne have been developed. In particular, there have been carried out a number of developments of drugs which directly act on *Propionibacterium acnes* that is a pathogen of acnes.

In 2004, the complete genome sequence of *Propionibacterium acnes* was determined. This clarified that many genes of *Propionibacterium acnes* encode a virulence factor (See Non-patent Literature 1). Based on this information, researches on sialidase of *Propionibacterium acnes* have been carried out in developing vaccine (See Non-patent Literature 2). In Non-patent Literature 2, inflammation is reproduced within mouse auricle skin.

CITATION LIST

Non-Patent Literature 1

Bruggemann H. et al, "The Complete Genome Sequence of *Propionibacterium Acnes*, a Commensal of Human Skin", Science, 2004, 305, 671-673.

Non-Patent Literature 2

Nakatsuji T. et al, "Vaccination Targeting a Surface Sialidase of *P. acnes*: Implication for New Treatment of Acne Vulgaris", PLoS ONE, 2008, 3, 2, 1-9.

SUMMARY OF INVENTION

Technical Problem

Most drugs that have been developed so far act on bacterial cells themselves of *Propionibacterium acnes* that are a cause of acnes and exert an anti-inflammatory effect. Accordingly, in a case where reinfection with *Propionibacterium acnes* occurs, inflammation occurs again. Further, even if the use of such drugs is effective temporarily, the use of the drugs induces emergence of a drug-resistant bacterium. This makes the treatment more difficult.

The present invention was made in view of the foregoing problems. An object of the present invention is to provide a compound which enables a continuous treatment of acne.

Solution to Problem

What can be expected as a continuous treatment on acne is immunotherapy, that is, a vaccine. Once effective anti-acne immunity is established (recognition and immunologic memory of specific *Propionibacterium acnes*), *Propionibacterium acnes* is immediately eliminated at least on reinfection with strains of the same *Propionibacterium acnes*. Accordingly, immunotherapy is expected to exert a continuous anti-inflammatory effect.

As a result of diligent studies, inventors of the present invention found out that inflammation can be induced more effectively by injection of *Propionibacterium acnes* in abdominal midline skin of mice than by injection in auricle skin of mice. By using this induction of inflammation, the inventors found that a peptide consisting of an amino acid sequence that could not have been arrived at based on conventional techniques can very efficiently suppress inflammation induced by *Propionibacterium acnes*, and achieved the present invention.

In order to solve the foregoing problems, a peptide of the present invention is a peptide, selected from the group consisting of: (a) a peptide consisting of an amino acid sequence indicated by SEQ NO. 1; and (b) a peptide consisting of an amino acid sequence derived from the amino acid sequence indicated by SEQ NO. 1 by deletion, substitution, insertion, or addition of one or several amino acids, the peptide suppressing, by immune response, inflammation caused by infection with *Propionibacterium acnes*.

Use of the peptide of the present invention enables suppressing inflammation (acne and pimple) caused by infection with *Propionibacterium acnes*.

In order to solve the foregoing problems, a peptide of the present invention may be a peptide, selected from the group consisting of: (c) a peptide consisting of an amino acid sequence indicated by SEQ NO. 3; and (d) a peptide consisting of an amino acid sequence derived from the amino acid sequence indicated by SEQ NO. 3 by deletion, substitution, insertion, or addition of one or several amino acids, the peptide suppressing, by immune response, inflammation caused by infection with *Propionibacterium acnes*.

A peptide composition of the present invention may be a peptide composition including: (e) the peptide described in the above (a) or (b), or a peptide which is in a form of a multivalent antigen peptide obtained by binding a plurality of peptides described in the above (a) or (b) by a linker; and (f) the peptide described in the above (c) or (d), or a peptide which is in a form of a multivalent antigen peptide obtained by binding a plurality of peptides described in the above (c) or (d) by a linker.

A vaccine of the present invention is a vaccine against *Propionibacterium acnes*, including the above peptide or the above peptide composition.

A polynucleotide of the present invention is a polynucleotide encoding the above peptide.

An expression vector of the present invention is an expression vector to which the above polynucleotide is operably linked. Use of the expression vector of the present invention enables providing a peptide which can suppress inflammation caused by infection with *Propionibacterium acnes*.

An antibody of the present invention is an antibody which specifically recognizes the above peptide.

A method of the present invention for determining effectiveness of a vaccine against *Propionibacterium acnes* includes the step of detecting whether a polynucleotide encoding the above peptide exists in a sample gathered from a living body. Use of the method of the present invention enables easily determining whether the vaccine against *Propionibacterium acnes* is effective in a living body or not, before administering the vaccine to the living body.

A method of the present invention for treating or preventing inflammation caused by *Propionibacterium acnes* includes the step of administering to an individual the above vaccine, the vaccine containing a therapeutically effective amount of the peptide.

A method of the present invention for treating or preventing inflammation caused by *Propionibacterium acnes* includes the step of administering to an individual the above vaccine, the vaccine containing a therapeutically effective amount of the polynucleotide.

Advantageous Effects of Invention

A peptide of the present invention has a very high antigenicity. Therefore, the use of the peptide of the present invention can provide a vaccine against *Propionibacterium acnes*.

BRIEF DESCRIPTION OF DRAWINGS

FIG. 4 is a diagram showing a result of examining anti-inflammatory effects of peptides.

FIG. 5 is a diagram showing another result of examining anti-inflammatory effects of peptides.

FIG. 6 is a diagram comparing a 16S rDNA base sequence of a strain isolated from a patient and a 16S rDNA base sequence of a standard strain.

DESCRIPTION OF EMBODIMENTS

[Peptide and Polynucleotide]

Figure 1:
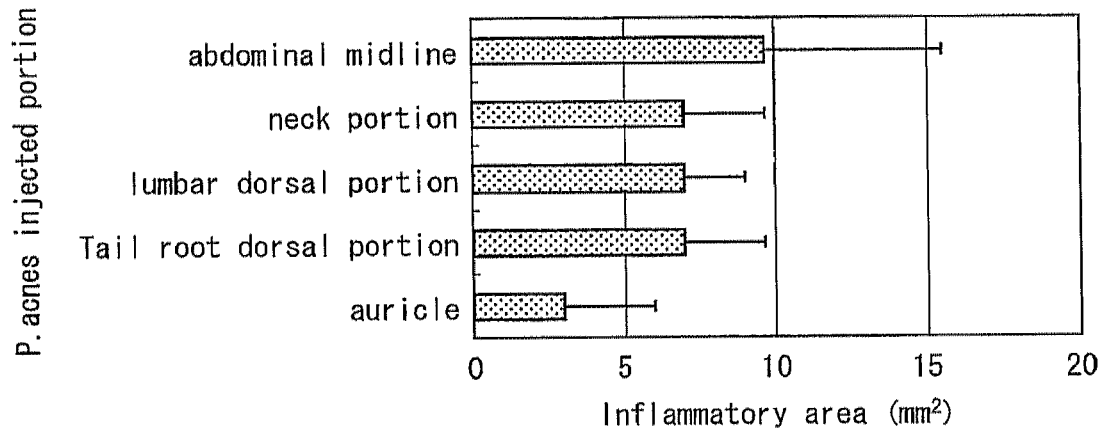
FIG. 1 is a diagram showing a result of measuring inflammatory areas caused by injection of *Propionibacterium acnes* into individual portions.

The present invention provides an antigen peptide that is capable of inducing an immune response against *Propionibacterium acnes* infection.

In one aspect, the present invention may be one of peptides (a) to (d) as follows:

(a) a peptide consisting of an amino acid sequence indicated by SEQ NO. 1;

(b) a peptide consisting of an amino acid sequence derived from the amino acid sequence indicated by SEQ NO. 1 by deletion, substitution, insertion, or addition of one or several amino acids, the peptide generating, by immune response, an antibody suppressing an increase of *Propionibacterium acnes*;

(c) a peptide consisting of an amino acid sequence indicated by SEQ NO. 3; and (d) a peptide consisting of an amino acid sequence derived from the amino acid sequence indicated by SEQ NO. 3 by deletion, substitution, insertion, or addition of one or several amino acids, the peptide generating, by immune response, an antibody suppressing an increase of *Propionibacterium acnes*.

Here, the "several amino acids" can be, for example, two or three amino acids, and more preferably, two amino acids.

In a case where an amino acid is substituted, preferable substitution is substitution of one amino acid for another amino acid that has the same properties as the one amino acid, such as substitution of one amino acid for another amino acid that has the same side-chain functional group as the one amino acid (e.g. substitution of Arg for Lys and substitution of Asp for Glu); and substitution of one hydrophobic amino acid for another hydrophobic amino acid (e.g. substitution of Val for Ile).

In the present specification, the term "peptide" is used in a manner exchangeable with "polypeptide" or "protein".

The peptide consisting of the amino acid sequence indicated by SEQ NO. 1 corresponds to amino acid residues from 90th amino acid residue to 103rd amino acid residue in a membrane protein of *Propionibacterium acnes* which consists of an amino acid sequence registered in Genbank/EMBL/DDBJ with the Accession No. AAT84059. The peptide consisting of the amino acid sequence indicated by SEQ NO. 3 corresponds to amino acid residues from 260th amino acid residue to 272nd amino acid residue in a membrane protein of *Propionibacterium acnes* which consists of an amino acid sequence registered in Genbank/EMBL/DDBJ with the Accession No. YP_056445. The proteins consisting of the amino acid sequences registered in the above Accession Nos. are proteins that are supposed, as a result of genome analysis described in Non-patent Literature 1, to be expressed. In general, in production of antibodies, an amino acid sequence excellent as an antigen is a hydrophilic amino acid sequence and an amino acid sequence having abundant charges and also an amino acid sequence that is predicted to have a turn structure. The charges may be either positive or negative and it is desirable to include at least five charged amino acids. Further, the length of a selected amino acid preferably corresponds 10 to 15 residues. The amino acid sequence indicated by SEQ NO. 1 or 3 is selected based on the above idea.

These peptides induce immunity to *Propionibacterium acnes* that is xenobiotic. It is inferred that at the induction of immunity, production of specific antibody is induced as a result of induction of Th2 dominated immunity.

A method of producing a polypeptide of the present invention may be chemical synthesis or may employ an expression vector. In the case of chemical synthesis, the peptide of the present invention can be produced by a well-known method of synthesizing a peptide. As examples of the method of synthesizing a peptide, there are a chemical synthesis method such as a liquid peptide synthesis method and a solid phase peptide synthesis method. However, the method is not limited to these. In the case of employing an expression vector, a peptide may be produced from a transformant to which an expression vector has been introduced or may be produced using an in vitro translation system. For example, a polynucleotide encoding the peptide (e.g. polynucleotide including a base sequence indicated by SEQ NO. 2 or 4) is inserted into an expression vector and the expression vector is introduced into a host cell, so that a target peptide can be produced in the host cell. The term "transformant" used herein indicates not only a cell, a tissue, and an organ, but also a living organism itself. A method for preparing a transformant may be a procedure well known in this field, such as transformation by introducing a recombinant vector into a host. Examples of a living organism to be transformed include, but not limited to, microorganisms, plants, and animals. Whether a gene has been introduced into a host cell or not may be confirmed by a procedure well known in this field, such as PCR, Southern hybridization, Northern hybridization etc.

In the case of producing the peptide of the present invention by preparing a transformant, it is preferable that the peptide is expressed stably in a host cell. However, the peptide may be expressed transiently in a host cell. The peptide thus produced may be purified by a publicly known method. Examples of the method for purifying the peptide include, but not limited to, gel filtration chromatography, ion exchange chromatography, and affinity chromatography.

In another aspect, the peptide of the present invention may be in the form of a multivalent antigen peptide (which may be also referred to as MAP: Multiple Antigen Peptide) obtained by binding a plurality of peptides (a) or (b) below or by binding a plurality of peptides (c) or (d) below via a linker.

(a) a peptide consisting of an amino acid sequence indicated by SEQ NO. 1;

(b) a peptide consisting of an amino acid sequence derived from the amino acid sequence indicated by SEQ NO. 1 by deletion, substitution, insertion, or addition of one or several amino acids, the peptide generating, by immune response, an antibody suppressing an increase of *Propionibacterium acnes;*

(c) a peptide consisting of an amino acid sequence indicated by SEQ NO. 3; and (d) a peptide consisting of an amino acid sequence derived from the amino acid sequence indicated by SEQ NO. 3 by deletion, substitution, insertion, or addition of one or several amino acids, the peptide generating, by immune response, an antibody suppressing an increase of *Propionibacterium acnes.*

MAP is a peptide capable of showing a higher antigenicity, and is a multivalent peptide obtained by adding a linker to a C-terminus of a specific peptide and binding via the linker the specific peptide with a MAP structure (matrix) constructed based on Lys. MAP may be synthesized by a conventional and publicly known method. The number of specific peptides to be included in one MAP molecule is not particularly limited, but is preferably 5 or more. The upper limit of the number of specific peptides to be included in one MAP molecule is not limited since the number is preferably large in terms of antigenicity. In terms of restriction due to synthesis technique at present, MAP may be produced with the number of specific peptides being 15 molecules or less.

In general, a Cys residue is used as an amino acid constituting a linker to be added to a specific peptide. However, in the peptide in the form of MAP of the present invention, there is used a linker including a Gly residue between a specific peptide and a Cys residue. Specifically, -GlyCys or -GlyGlyCys is added as a linker to a C-terminus of the specific peptide. For example, -GlyCys is added to a C-terminus of a peptide consisting of the amino acid sequence indicated by SEQ NO. 1, and -GlyGlyCys is added to a C-terminus of a peptide consisting of the amino acid sequence indicated by SEQ NO. 3. Since the Gly residue is added between the Cys residue and the C-terminus of the specific peptide, the Cys residue is given flexibility in rotation so that when binding to the MAP structure, the specific peptide does not suffer steric hindrance and the Cys residue at the linker can form an angle which enables the Cys residue to be close to a MAP reactive group. The linker for the peptide of the present invention in the form of MAP is not limited to this, and may be a general linker constituted by the Cys residue.

In another aspect, the peptide of the present invention is provided in the form of a peptide composition containing a peptide (e) or (f) below.

(e) the peptide (a) or (b), or a peptide in the form of a multivalent antigen peptide obtained by binding a plurality of the peptides (a) or (b) via a linker; and (f) the peptide (c) or (d), or a peptide in the form of a multivalent antigen peptide obtained by binding a plurality of the peptides (c) or (d) via a linker.

"Composition" used herein indicates a substance containing a plurality of components.

A ratio of mixing individual components is not particularly limited and may be 1:1 (weight ratio) for example. Further, in order to ensure higher immunogenicity, the peptide composition preferably includes: a peptide in the form of a multivalent antigen peptide obtained by binding via a linker a plurality of peptides consisting of the amino acid sequence indicated by SEQ NO. 1; and a peptide in the form of a multivalent antigen peptide obtained by binding via a linker a plurality of peptides consisting of the amino acid sequence indicated by SEQ NO. 3.

Further, the present invention provides a polynucleotide encoding the peptides (a)-(d). Examples of the polynucleotide of the present invention include, but not limited to, a polynucleotide consisting of a base sequence indicated by SEQ NO. 2 or 4. The term "base sequence" used herein is exchangeable with "nucleic acid sequence" or "nucleotide sequence", and is indicated as a sequence of deoxyribonucleotides (abbreviated as A, G, C, and T). The base sequence indicated by SEQ NO. 2 encodes the peptide consisting of the amino acid sequence indicated by SEQ NO. 1, and the base sequence indicated by SEQ NO. 4 encodes the peptide consisting of the amino acid sequence indicated by SEQ NO. 3.

The polynucleotide of the present invention may be in the form of DNA or RNA. A person skilled in the art can easily produce the polynucleotide of the present invention based on amino acid sequence information of the peptide of the present invention and base sequence information encoding the peptide. Specifically, the polynucleotide of the present invention can be produced by general DNA synthesis, PCR etc.

Further, the present invention provides a vector containing the polynucleotide encoding the peptide. When the vector is used in production of the peptide, it is preferable that the vector is an expression vector to which the polynucleotide is operably linked. The wording "operably linked to" used herein indicates that a polynucleotide for encoding a target peptide is under the control of a control region such as a promoter and is capable of expressing the peptide in a host cell. A procedure for causing a polynucleotide encoding a target peptide to be "operably linked" to an expression vector so as to construct a desired vector is well known in the art. Further, the technique of introducing an expression vector into a host cell is also well known in the art. Accordingly, a person skilled in the art can easily produce a desired peptide in a host cell.

Use of the peptide of the present invention and the polynucleotide of the present invention enables inducing immunity to *Propionibacterium acnes*. That is, the peptide of the present invention and the polypeptide of the present invention can serve as vaccines against *Propionibacterium acnes*. Accordingly, use of the peptide of the present invention and the polynucleotide of the present invention enables subduing intradermic inflammation (e.g. acne and pimple) due to *Propionibacterium acnes*.

[Vaccine]

A vaccine of the present invention is a vaccine against *Propionibacterium acnes*, and contains the aforementioned peptide, the aforementioned peptide composition, or the aforementioned polynucleotide as an effective component. The term "vaccine" used herein indicates a vaccine which is used for immunotherapy (vaccine therapy) and which induces an immune response specific to the peptide of the present invention.

The vaccine of the present invention may be provided in the form of a vaccine composition or in the form of a vaccine kit. Herein, "a vaccine composition containing an effective component" and "a vaccine kit containing an effective component" are generically referred to as "a vaccine containing an effective component". "Kit" indicates a form in which individual components are contained in different substances such that at least one component is contained in one substance and the rest is contained in another substance. The vaccine composition and the vaccine kit will be detailed later.

In general, the term "composition" indicates "a substance in which two or more components exist evenly as a whole so that the components are considered as one substance". A composition may be, for example, a single substance containing a material A as a main component, or a single substance containing materials A and B as main components. That is, administration of the vaccine of the present invention may be, for example, single administration of a peptide consisting of the amino acid sequence indicated by SEQ NO. 1 or a peptide consisting of the amino acid sequence indicated by SEQ NO. 3, or may be administration of a mixture of these two peptides. In a case of administrating the mixture of the two peptides, even if an amino acid sequence of an antigen protein of *Propionibacterium acnes* which antigen protein corresponds to one of the two peptides is mutated and the anti-inflammatory effect of the one peptide is lost, the other peptide can exert the anti-inflammatory effect. Such a composition may contain other component (e.g. support which is pharmaceutically acceptable) in addition to the materials A and B. The vaccine composition of the present invention contains a later-mentioned effective component as the material A or B, and may be used alone or used in combination with other material or other composition. In the latter case, the material or the composition to be used in combination with vaccine composition of the present invention may be or may not be contained in the vaccine composition of the present invention. When such material or composition is not contained in the vaccine composition of the present invention, a combination of such material or composition and the vaccine composition of the present invention cannot be recognized as one composition, but can be encompassed in the "kit" and can be provided as a kit. A person skilled in the art can easily understand this.

In one aspect, the present invention provides a vaccine composition. In one embodiment, the vaccine composition of the present invention contains the peptide of the present invention. In another embodiment, the vaccine composition of the present invention contains the polynucleotide of the present invention. In the present embodiment, the polynucleotide of the present invention is preferably in the form capable of expressing the peptide encoded by the polynucleotide of the present invention, and is more preferably provided in the form of an expression vector to which the polynucleotide of the present invention is operably linked. As described above, the peptide of the present invention or the polynucleotide of the present invention is used as an effective vaccine component in preparing a vaccine against *Propionibacterium acnes*.

The vaccine of the present invention can be used as a prophylactic vaccine or a therapeutic vaccine against *Propionibacterium acnes*. The term "prophylactic vaccine" used herein indicates a vaccine administered to an untreated individual in order to prevent the individual from being infected with a disease. The term "therapeutic vaccine" used herein indicates a vaccine administered to an individual already infected with a disease in order to improve the infection or make the infection as small as possible or to eliminate the immunopathological effect of the disease.

How to prepare a vaccine containing an effective component is well known by a person skilled in the art. A representative example of the vaccine of the present invention is prepared as an injectable which is either a solution or a suspension. Alternatively, the vaccine of the present invention may be prepared in an appropriate solid form to be solved or suspended in a solution before injection. Such preparation may be emulsified or may be a protein emulsified in a ribosome.

The effective component of the vaccine composition of the present invention may be mixed with a diluent which is pharmaceutically acceptable and is compatible with the effective component. Preferable examples of the diluent include water, physiological saline, dextrose, glycerol, ethanol, and mixtures thereof. Further, if desired, the vaccine composition of the present invention may contain a little amount of an assisting substance such as a wetting agent or emulsifier and pH buffer.

The vaccine composition of the present invention may be administered by injection (including intradermic one, hypodermic one, and intramuscular one) via various routes (e.g. nasal cavity, mucosa, oral, intravaginal, urethra, and intraocular) or may be non-orally administered using a patch (endermic administration), a suppository etc.

The vaccine composition of the present invention may be administered orally. In the case of the oral administration, the vaccine composition of the present invention is used in combination with a diluent such as pharmaceutical-grade mannitol, lactose, starch, magnesium stearate, sodium saccharate, cellulose, and magnesium carbonate. The vaccine composition of the present invention when administered orally may be in the form of a solution, a suspension, a tablet, a pill, a capsule, a sustained release formulation, or a powder medicine. In a case where the vaccine composition of the present invention is provided in a freeze-dried form, the freeze-dried substance may be reconstructed as a suspension before administration. The reconstruction is preferably carried out in a buffer solution.

The vaccine composition of the present invention may contain an adjuvant for enhancing effectiveness of the vaccine. Examples of the effective adjuvant include, but not limited to, aluminum hydroxide, aluminum phosphate, aluminum potassium sulfate (alum), beryllium sulfate, silica, kaoline, carbon, water-in-oil type emulsion, oil-in-water type emulsion, Muramyl dipeptide, bacterial endotoxin, fat X, *Bordetella pertussis*, *Corynebacterium parvum*, polyribonucleotide, sodium alginate, lanoline, lysolecithin, vitamin A, sponin, liposome, levamisole, DEAE-dextran, block copolymer, and other synthesized adjuvant. These adjuvants are commercially available from various suppliers. Representative examples of these adjuvants include an oil-in-water type adjuvant, an aluminum hydroxide adjuvant, and an adjuvant mixed with these adjuvants. An adjuvant which is permitted to be applied to humans is aluminum hydroxide.

In another aspect, the present invention provides a vaccine kit. The vaccine kit of the present invention corresponds to the aforementioned vaccine composition, and may contain the peptide of the present invention or the polynucleotide of the present invention as an effective vaccine component, and may further contain a component of the aforementioned vaccine composition.

In one embodiment, the vaccine kit of the present invention contains the peptide of the present invention. In another embodiment, the vaccine kit of the present invention contains the polynucleotide of the present invention. In the present embodiment, the polynucleotide of the present invention is preferably in the form capable of expressing the peptide encoded by the polynucleotide of the present invention, and is more preferably provided in the form of an expression vector to which the polynucleotide of the present invention is operably linked.

The term "kit" used herein indicates a package including a container (e.g. bottle, plate, tube, and dish) containing therein a specific material. The kit preferably has directions for using individual materials. The term "includes (including)" used in the aspect of the kit in the present specification indicates that a material is contained in any one of individual containers constituting the kit. Further, the kit of the present invention may be a package in which a plurality of different compositions are contained. The form of the composition may be as above, and if the composition is in the form of a solution, the composition may be contained in a container. The kit of the present invention may be designed such that materials A and B are mixed and included in a single container or are included in respective containers. The "directions" may be written on a paper or other kind of a medium or may be printed out. Alternatively, the "directions" may be in the form of a magnetic tape or an electronic medium such as a computer-readable disc or tape and a CD-ROM. Further, the kit of the present invention may include a container containing a diluent, a solvent, a cleaning liquid, or other reagent. Further, the kit of the present invention may include beforehand an instrument necessary for prevention/treatment of acne caused by infection with *Propionibacterium acnes*.

Use of the vaccine of the present invention as above enables efficiently preventing/treating inflammation (acne) caused by infection with *Propionibacterium acnes*.

That is, a method for treating or preventing inflammation caused by *Propionibacterium acnes*, including the step of administering to an individual a vaccine containing a therapeutically effective amount of the peptide of the present invention or a therapeutically effective amount of the polynucleotide of the present invention, is also encompassed in the present invention.

The term "therapeutically effective amount" used herein indicates the amount of peptide or polynucleotide which amount enables the peptide or the polynucleotide to exert a desired therapeutic effect or prophylactic effect. The therapeutically effective amount may differ depending on the age, the weight, and other health conditions of an individual to which the vaccine is administered, on the condition of an inflammation to be treated, and on a method of administration. In a case of subcutaneous administration, one example may be administration of a vaccine made in such a manner that 5-10 µg of the peptide per kg weight or 10-50 µg of the polynucleotide per kg weight is supplied in one administration. In order to induce an immune response sufficient for anti-inflammation, the vaccine may be administered two times or more to an individual. In this case, administration is made at a predetermined interval.

Another example is as follows: in a case of a vaccine containing a mixture of MAP based on the peptide consisting of the amino acid sequence indicated by SEQ NO. 1 and MAP based on the peptide consisting of the amino acid sequence indicated by SEQ NO. 3 (weight ratio is 1:1), administration may be made via hypodermic injection in such a manner that 100-500 µg of each peptide per one shot is administered in the form of a physiological saline solution five times or so at an interval of 3-5 days.

In a case of administration via a patch, one dose may be small, the number of dose may be reduced, and an individual can treat himself/herself using the patch.

The term "individual" used herein indicates individual humans and mammals other than humans (such as rats, mice, rabbits, pigs, cattle, and monkeys).

[Antibody]

The present invention provides an antibody which specifically recognizes any of the peptides of the present invention. That is, an antibody of the present invention can specifically bind to any of the peptides. In one embodiment, the antibody of the present invention is preferably an antibody which binds to (1) the peptide consisting of the amino acid sequence indicated by SEQ NO. 1 or 3 or (2) a multivalent antigen peptide synthesized by the MAP process from the peptide consisting of the amino acid sequence indicated by SEQ NO. 1 or 3.

The term "antibody" used herein indicates an immunoglobulin (IgA, IgD, IgE, IgG, IgM, and Fab fragments thereof, F(ab')$_2$ fragment and Fc fragment). Examples of the antibody include, but not limited to, polyclonal antibodies, monoclonal antibodies, single-chain antibodies, and antiidiotype antibodies.

The antibody of the present invention may be produced by a method well known in the field to which the present invention pertains. For example, the antibody can be obtained by administering the peptide of the present invention to a living body of a mammal and causing an immune response so that an antibody is produced in the living body. The antibody obtained in this case is generally a polyclonal antibody. A monoclonal antibody can be produced by a conventional and publicly known hybridoma technique etc. using the peptide of the present invention. Alternatively, the monoclonal antibody can be produced by application of a recombinant DNA technique or chemical synthesis.

Use of the antibody of the present invention enables easily purifying the peptide of the present invention. For example, by subjecting the peptide of the present invention expressed in a cell using the vector of the present invention or the transformant of the present invention to affinity purification using the antibody of the present invention, it is possible to efficiently collect the peptide.

The antibody of the present invention may be any antibody as long as the antibody specifically binds to the peptide of the present invention, and should not be limited in terms of the kinds of individual immunogloblins (IgA, IgD, IgE, IgG, or IgM), a method for preparing a chimeric antibody, a method for preparing a peptide antigen etc. which are specifically described in the present specification. Therefore, it should be noted that an antibody obtained by a method other than the above methods is also encompassed in the present invention.

[Method for Determining Effectiveness of Vaccine]

A method of the present invention for determining effectiveness of a vaccine against *Propionibacterium acnes* is only required to include a detection step of detecting whether a polynucleotide encoding the above peptide exists or not in a sample collected from a living body, and is not particularly limited in terms of other specific steps and instruments and devices to be used.

In a case where a polynucleotide encoding the peptide is detected in the detection step, it can be determined that administration of the vaccine of the present invention to a test subject is highly likely to result in efficient suppression of inflammation caused by *Propionibacterium acnes*. Specifically, when the polynucleotide encoding the above peptide is detected, it is determined that the vaccine of the present invention is likely to be effective against *Propionibacterium acnes*.

The method for detecting the polynucleotide encoding the peptide is not particularly limited. For example, the method may be detection by PCR amplification or detection by determining a base sequence of a PCR product. By determining the base sequence of the PCR product, it is possible to determine more accurately whether a vaccination effect can be exerted or not. Whether the vaccination effect can be exerted or not may be determined also depending on whether a PCR fragment is generated or not by amplification. For example, in a case where a fragment with a desired length is generated by amplification. Using a specific primer for amplifying the above polynucleotide (in a case where the result of PCR detection is positive), it is highly possible that the test subject is infected with *Propionibacterium acnes* retaining the above polynucleotide, and so it is determined that the vaccination effect is highly expected. On the other hand, in a case where a fragment with a desired length is not generated (in a case where the result of PCR detection is negative), it is determined that the vaccination effect is expected little. Before PCR amplification, *Propionibacterium acnes* that can be contained in a sample collected from the test subject may be grown by culturing the sample.

A method for determining whether the vaccine of the present invention against *Propionibacterium acnes* is to be used or not may be made by detecting whether a partial sequence of 16S rDNA of *Propionibacterium acnes* in a sample collected from a living body exists or not. Detection of whether the partial sequence of 16S rDNA exists or not may be detection by PCR amplification and detection by determining a base sequence of a PCR product. This determination may indicate that the inflammation of the test subject is derived from *Propionibacterium acnes*. This may be a basis for using the vaccine.

A model animal which is a mammal other than humans, such as mice in later-mentioned Examples, whose abdominal midline was intradermically injected with *Propionibacterium acnes* with predetermined bacterial cell concentration or more to cause inflammation of *Propionibacterium acnes*, and a method for preparing the model animal, are also encompassed in the present invention. In the model animal, inflammation of *Propionibacterium acnes* is created in a more efficient manner than a conventional method for creating inflammation. A determination system having been used so far in developing an anti-acne drug is a one based on the assumption that the drug is applied. Consequently, in developing a vaccine, there has been constructed so far no assured determination system which can determine the effect of the vaccine in vivo. The method for determining effectiveness of the vaccine, the model animal, and the method for preparing the model animal can be preferably used in developing a vaccine against *Propionibacterium acnes*.

The following explains embodiments of the present invention in more detail, with reference to Examples. It should be noted that the present invention is not limited to the Examples below and may be modified in terms of its details. The present invention is not limited to the description of the embodiments above, but may be altered by a skilled person within the scope of the claims. An embodiment based on a proper combination of technical means disclosed in different embodiments is encompassed in the technical scope of the present invention. All the documents cited in the specification are incorporated by reference.

EXAMPLES

Example 1

Culture of *P. acnes*

Strains of *Propionibacterium acnes* (hereinafter abbreviated as "*P. acnes*") (ATCC6919) were purchased from RIKEN BioResource Center (JCM catalogue No. 6425). The strains of the purchased *P. acnes* were cultured according to culture condition information from the center. Specifically, in an anaerobic glove box, the strains of the *P. acnes* were suspended in 100 ml of a GAM culture medium (manufactured by Nippon Suisan Kaisha, Ltd.) and cultured anaerobically using a vial at 37° C. for three days.

Example 2

Causing Intradermical Inflammation in Mouse Skin by *P. acnes*

Living bacterial cells of *P. acnes* were put in a deaerated physiological saline while keeping an anaerobic condition to prepare a suspension with the number of the living bacterial cells of *P. acnes* of $5 \times 10^7$ cells/ml, $1 \times 10^8$ cells/ml, or $5 \times 10^8$ cells/ml. The anaerobic condition was kept by spraying a nitrogen gas. The number of the living bacterial cells of *P. acnes* was calculated based on the assumption that OD measurement value of 0.98-1.02 at 550 nm measured by a spectrophotometer corresponds to $5 \times 10^8$ cells/ml, with reference to Non-patent Literature: Ramstad S et al., Photochem. Photobiol. Sci., 2006, 5, 66-72.

50 μl of the prepared suspension of *P. acnes* was intradermically injected into shaven abdominal midlines, neck portions, lumbar dorsal portions, tail root dorsal portions, and auricles of male Balb/c mice (9-10 weeks old). The inflammatory areas (major axis×minor axis: mm$^2$) at individual portions to which the suspension was injected intradermically were measured at predetermined times. Each group consisted of five individuals.

Figure 2:
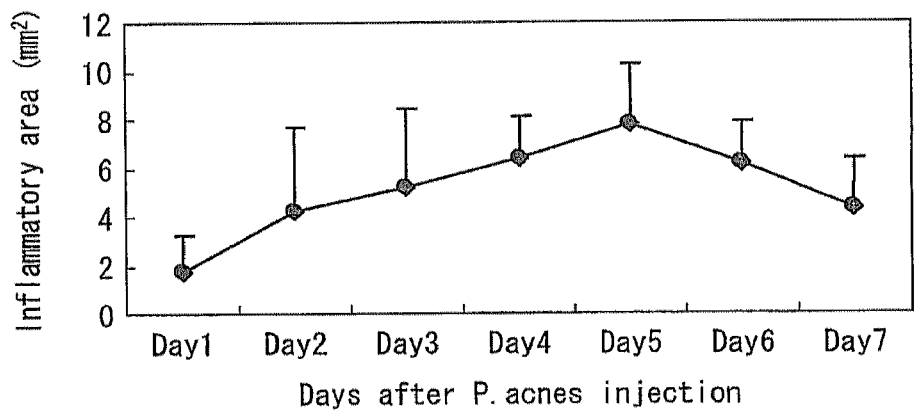
FIG. 2 is a diagram showing a relation between an inflammatory area caused by injection of *Propionibacterium acnes* and elapsed time after the injection.

As a result, in a group to which the suspension of *P. acnes* whose bacterial cell concentration was $5 \times 10^8$ cells/ml was injected, inflammation was apparently confirmed. FIG. 1 is a graph showing the result of inflammatory areas at individual portions observed 5 days after the injection. As illustrated in FIG. 1, inflammation was observed in individual portions to which the suspension was intradermically injected, and the inflammatory area was largest at an intradermic portion of the abdominal midline. That is, when causing intradermic inflammation of mice, intradermic injection into the abdominal midline was most effective. Inflammation at the auricle was the mildest among the observed portions. FIG. 2 is a graph showing the result of the inflammatory area at the abdominal midline at individual times after the suspension was intradermically injected into of the abdominal midline. As illustrated in FIG. 2, the inflammatory area at the abdominal midline was largest 5 days after the injection of *P. acnes*.

In contrast thereto, in the groups to which the suspensions of *P. acnes* whose bacterial cell concentrations were $5 \times 10^7$ cells/ml and $1 \times 10^8$ cells/ml, respectively, were injected, no inflammation could be caused at any portions and at any times.

Example 3

Preparation of Peptide

The powder of PepA which was a peptide consisting of the amino acid sequence indicated by SEQ NO. 1 or the powder of PepD which was a peptide consisting of the amino acid sequence indicated by SEQ NO. 3 was dissolved in physiological saline (produced by Otsuka Pharmaceutical Co., Ltd.) to prepare 800 μg/ml of a peptide solution.

As Comparative Examples, there were used PepB which was a peptide corresponding to 10th-26th amino acid residues in a membrane protein of *Propionibacterium acnes* which consists of the amino acid sequence registered in Genbank/EMBL/DDBJ accession No. AAT81852, and PepC which was a peptide corresponding to 145th-166th amino acid residues in a membrane protein of *Propionibacterium acnes* which consists of the amino acid sequence registered in Genbank/EMBL/DDBJ accession No. YP_055518. Table 1 shows information on the amino acid sequence in individual peptides. The sequences used as the Comparative Examples were amino acid sequences which may be strong candidates for antigens in producing antibodies, i.e. amino acid sequences which are abundant in hydrophilic amino acids and charges, and were selected from amino acid sequences with a turn structure. Further, the proteins consisting of the amino acid sequences registered in the above accession Nos. are proteins supposed to be expressed as a result of genome analysis described in Non-patent Literature 1 above.

TABLE 1

| Peptide names | Amino acid sequences | SEQ NO. | Accession No. of derived protein |
|---|---|---|---|
| PepA | $^{90}$AIQEKYGDDRERAG$^{103}$ | 1 | AAT84059 |
| PepB | $^{10}$GRKPDTNKRSWHRKAS R$^{26}$ | 11 | AAT81852 |
| PepC | $^{145}$IDQVREYRHRDDDDD EDPGEDG$^{166}$ | 12 | YP_055518 |
| PepD | $^{260}$KDADKDNPTYQKV$^{272}$ | 3 | YP_056445 |

Example 4

Anti-Inflammatory Effect of Peptide PepA Against Inflammation Caused by *P. acnes*

Figure 3:
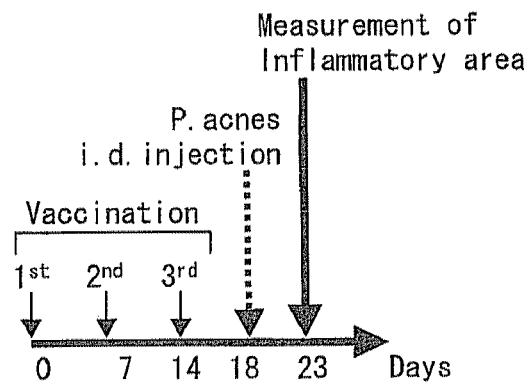
FIG. 3 is a diagram illustrating steps of examining anti-inflammatory effects of peptides.

In Example 2, the area of the inflammation caused by *P. acnes* was largest when 5 days had passed from intradermic injection of 50 μl of *P. acnes* ($5 \times 10^8$ cells/ml) into the abdominal midline. Accordingly, the anti-inflammatory effects of individual peptides were determined under the same conditions, i.e. by intradermically injecting 50 μl of *P. acnes* ($5 \times 10^8$ cells/ml) into the abdominal midline and measuring the inflammatory area (mm$^2$) 5 days after the injection. FIG. 3 illustrates the procedure for examining the anti-inflammatory effect.

FIG. 3 is a drawing schematically illustrating the procedure for examining the anti-inflammatory effect. As illustrated in FIG. 3, PepA (40 μg/50 μl/one individual) was intradermically vaccinated into dorsal portions of male Balb/c mice (7 weeks old at the first vaccination of PepA) 18 days before the injection of living bacterial cells of *P. acnes* (Day "0" in FIG. 3), 11 days before the injection (Day "7" in FIG. 3), and 4 days before the injection (Day "14" in FIG. 3), i.e. three times in total. Then, *P. acnes* was intradermically injected into the abdominal midlines of the mice, and the inflammatory areas were measured 5 days after the injection (Day "23" in FIG. 3). Each group consisted of 10 mice. As Comparative Examples, there were prepared a group of mice to which PBS without PepA was administered and a group of mice to which PepB or PepC was administered instead of PepA, and *P. acnes* was injected into the groups similarly. These results are shown in FIG. 4.

FIG. 4 is a graph showing the result of the anti-inflammatory effect of PepA. As illustrated in FIG. 4, the group to which PepA was administered exhibited a statistically significantly reduced inflammatory area (P=0.00865 (P<0.01)), compared with the control group to which PBS was administered. That is, PepA statistically significantly exhibits the anti-inflammatory effect against the inflammation caused by *P. acnes*. In the case of the group to which PepB was administered, P=1. In the case of the group to which PepC was administered, P=0.1655. These numerals were not significant statistically, and so it was considered that PepB and PepC do not exhibit the anti-inflammatory effect against the inflammation caused by *P. acnes*.

The above results show that the composition containing the peptide PepA is effective as a vaccine against *P. acnes*, i.e. an acne vaccine.

Example 5

Anti-Inflammatory Effect of Peptides PepA and PepD Against Inflammation Caused by *P. acnes*

The anti-inflammatory effects of individual peptides were examined using an inflammation causing system under the same conditions as in Example 4 except that the peptides to be administered to mice before injection of *P. acnes* were changed from PepA, PepB, and PepC to PepA and PepD. The results are shown in FIG. 5.

FIG. 5 is a graph showing the results of the anti-inflammatory effects of PepA and PepD. As shown in FIG. 5, the group to which PepA was administered exhibited a statistically significantly reduced inflammatory area (P=0.0012 (P<0.01)), compared with the control group to which PBS was administered, as in the result of Example 4. Further, the group to which PepD was administered exhibited a statistically significantly reduced inflammatory area (P=0.00175 (P<0.01)), compared with the control group to which PBS was administered.

The above results show that the composition containing the peptide PepA or PepD is effective as a vaccine against *P. acnes*, i.e. an acne vaccine.

Example 6

Identification of Strain Harbored by Acne Patient

[Extraction of 16S rDNA]

Purulence collected from a diseased part of an acne patient was cultured anaerobically on a GAM flat plate agar medium at 37° C., and a part of the bacterial cells was collected. The collected bacterial cells were transferred to a GAM flat plate agar medium and cultured anaerobically so that a single colony was produced. Bacterial cells from the single colony were collected, and suspended in a 20 mM NaOH aqueous solution. The suspension was heated at 94° C. for 3 min, the bacterial cells were lysed, and 16S rDNA was extracted. Using the extracted 16S rDNA, a base sequence of 16S rDNA of the bacterial cells with which the patient was infected was determined. The base sequence was determined with respect to each of three sets of bacterial cells collected from three acne patients, respectively.

[Determination of Base Sequence of 16S rDNA]

The extracted 16S rDNA was used as a template DNA. Further, as a primer, there were used primer 9F (forward primer): 5'-GTTTGATCCTGGCTCA-3' (SEQ NO. 5) and primer 800R (reverse primer): 5'-TACCAGGG-TATCTAATCC-3' (SEQ NO. 6). PCR carried out here consisted of 30 cycles each consisting of a step at 94° C. for 30 sec, a step at 55° C. for 60 sec, and a step at 72° C. for 60 sec. The PCR was carried out by AmpliTaq Gold DNA Polymerase (manufactured by Applied Biosystems). After the reaction, a PCR product was purified. Subsequently, a cycle sequence reaction was carried out using the purified PCR product. A product obtained in the cycle sequence reaction was purified, supplied to an ABI PRISM 310 Genetic Analyzer System (manufactured by Applied Biosystems), and a base sequence was determined using analysis software BioEdit. The primers used in the cycle sequence reaction were the above primer 9F and primer 536R: 5'-GTATTACCGCGGCT-GCTGG-3' (SEQ NO. 7). The cycle sequence reaction consisted of 25 cycles each consisting of a step at 96° C. for 10 sec, a step at 50° C. for 5 sec, and a step at 60° C. for 4 min.

[Result of Determining Base Sequence]

The result of determining the base sequence showed that in each of three separated bacterial strains that were established, derived from patients (patient strains 1-3), the base sequence of 16S rDNA at an amplified part (SEQ NO. 16) had the same sequence as that of the corresponding base sequence in ATCC6919 strain of *P. acnes* (SEQ NO. 8). FIG. 6 shows the result with respect to the patient strain 1. Accordingly, the three separated bacterial cells derived from the patients were identified as *P. acnes*.

Example 7

Anti-Inflammatory Effect of Peptide PepA Against Inflammation Caused by *P. acnes* Derived from Patient The anti-inflammatory effect of PepA was examined by the same procedure as in Example 5 except that bacterial cells of *P. acnes* to be injected into mice were the acne-patient-derived bacterial cells of *P. acnes* which were isolated in Example 6. The result is shown in FIG. 7.

Figure 7:
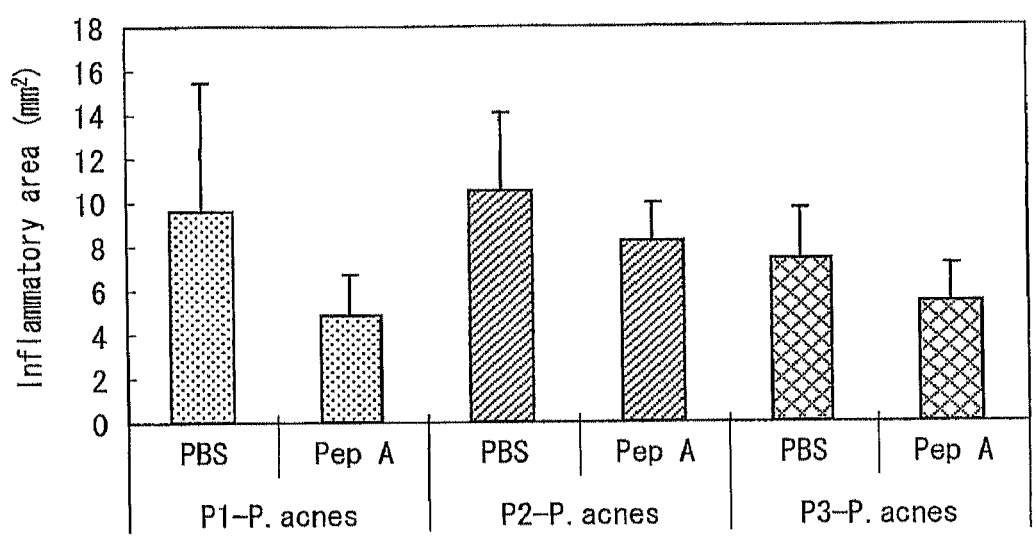
FIG. 7 is a diagram showing a result of examining anti-inflammatory effects of a peptide against injection of *Propionibacterium acnes* isolated from a patient.

FIG. 7 is a graph showing the result of intradermically injecting, after immunization by PepA, the patient strains 1-3 (P1-*P. acnes* to P3-*P. acnes*) to the abdominal midlines of mice and measuring inflammatory areas of the mice 5 days after the injection. As shown in FIG. 7, the group to which PepA was administered showed $P=0.0252$ ($P<0.05$) with respect to the patient strain 1, $P=0.0476$ ($P<0.05$) with respect to the patient strain 2, and $P=0.0237$ ($P<0.05$) with respect to the patient strain 3, compared with the control group to which PBS was administered instead of PepA. That is, administration of PepA enabled statistically significantly reducing an inflammatory area with respect to injection of each of the patient strains. This suggests that PepA is widely effective as an acne vaccine.

Example 8

Examination of Base Sequence Encoding PepA or PepD in *P. acnes* Derived from Acne Patient In order that PepA or PepD serves effectively as a vaccine, it is desirable that target *P. acnes* strains have a protein containing PepA or PepD. Accordingly, whether the target *P. acnes* strains had a protein containing PepA or PepD was examined by carrying out PCR and by determining and checking a base sequence of PCR products.

[Confirmation of PepA by PCR]

Primers used here for detecting a base sequence encoding an amino acid sequence of PepA were primer L: 5'-GAT-GAAAGCCATCCAGGAAA-3' (SEQ NO. 9) and primer R: 5'-GCACACGAAACAACGCTAGA-3' (SEQ NO. 10). PCR carried out here consisted of 35 cycles each consisting of a step at 95° C. for 15 sec, a step at 60° C. for 20 sec, and a step at 72° C. for 30 sec. The PCR was carried out using AmpliTaq Gold DNA Polymerase (manufactured by Applied Biosystems).

As a result, a PCR fragment with a desired length was obtained by amplification from the detected patient-derived *P. acnes*, and consequently existence of a base sequence encoding the amino acid sequence of PepA was deduced. This suggests that a protein corresponding to PepA has the same amino acid sequence as that of PepA.

Further, specimens collected from 21 volunteers were examined as to whether they had a base sequence encoding the amino acid sequence of PepA, and 19 cases out of 21 cases were positive. The term "positive" used in the present Examples indicates that a fragment with a desired length was generated by PCR amplification using a specific primer. The term "negative" used in the present Examples indicates that a fragment with a desired length could not be generated by PCR amplification using a specific primer.

Similarly, the specimens collected from the 21 volunteers were examined by PCR as to whether they had 16S rDNA of *P. acnes*. The result showed that the 19 cases being positive in examination of the base sequence encoding the amino acid sequence of PepA was also positive in examination of 16S rDNA, and the 2 cases being negative in examination of the base sequence encoding the amino acid sequence of PepA was also negative in examination of 16S rDNA. The results of the 2 cases being negative in PCR detection for confirming the base sequence encoding the amino acid sequence of PepA do not indicate that the base sequence encoding the amino acid sequence of PepA was not carried by the 2 volunteers but indicates that the number of bacterial cells of *P. acnes* was so low that the bacterial cells could not be detected. From the above results, it was suggested that a protein containing the amino acid sequence of PepA exists in the 19 cases in which 16S rDNA of *P. acnes* was confirmed.

TABLE 2

| Subjects | Total | Mean age | Mongoloid | Caucasoid | PCR positives (%) |
|---|---|---|---|---|---|
| Male | 4 | 25.75 | 2 | 2 | 4 (100) |
| Female | 15 | 29.43 | 14 | 1 | 15 (100) |
| Total | 19 | 28.61 | 16 | 3 | 19 (100) |
| PCR Positives (%) | 19 (100) | | 16 (100) | 3 (100) | |

Further, similarly as above, specimens collected from another 11 volunteers were examined by PCR as to whether they had 16S rDNA of *P. acnes*. The result showed that each of the specimens was *P. acnes* positive. Further, the 11 cases were examined as to whether they had a base sequence encoding the amino acid sequence of PepA and all of the 11 cases were found to be positive. Table 3 shows the results of the 11 cases together with the results of the 19 cases which were found to be positive.

TABLE 3

| Subjects | Total | Mean age | Mongoloid | Caucasoid | PCR positives (%) |
|---|---|---|---|---|---|
| Male | 7 | 25.86 | 5 | 2 | 7 (100) |
| Female | 23 | 29.55 | 22 | 1 | 23 (100) |
| Total | 30 | 28.66 | 27 | 3 | 30 (100) |
| PCR Positives (%) | 30 (100) | | 27 (100) | 3 (100) | 30 (100) |

[Confirmation of Base Sequences Encoding PepA and PepD]

With respect to each of specimens collected from 5 volunteers and *P. acnes* described in Example 1, DNA encoding the amino acid sequence of PepA and DNA encoding the amino acid sequence of PepD were amplified by PCR. In amplifying DNA encoding PepA, the primer L (SEQ NO. 9) and the primer R (SEQ NO. 10) were used as primers. In amplifying DNA encoding PepD, primer om1L: 5'-GGTGCTGTCGT-CAATAACAACTTC-3' (SEQ NO. 14) and primer om1R: 5'-GGAGTGGCCAGAGACGATCT-3' (SEQ NO. 15) were used as primers. PCR carried out here consisted of (i) a step at 95° C. for 5 min, thereafter (ii) 35 cycles each consisting of a step at 95° C. for 15 sec, a step at 53° C. for 20 sec, and a step at 72° C. for 30 sec, and thereafter (iii) a step at 72° C. for 7 min and a step at 25° C. for 10 min. Table 4 shows the result of PCR.

As shown in Table 4, in all the specimens, with respect to PepA, PCR products with a desired size were generated by amplification. The cases where the PCR products with a desired size were generated by amplification are shown as "positive". With respect to PepD, PCR products with a desired size were generated by amplification except for the specimen of the patient strain D.

Subsequently, base sequences of the PCR products were determined to determine deduced amino acid sequences. Determination of the base sequences was made by using 3130×1 Genetic Analyzer, Sequencing Analysis Software ver 5.3.1., and KB BaseCaller (each manufactured by Applied Biosystems). Table 4 shows the result. As shown in Table 4, in all the specimens, the sequence of PepA was conserved. That is, the deduced amino acid sequence thus obtained was the same as the amino acid sequence indicated by SEQ NO. 1. On the other hand, in the specimens of the patient strains C and E, the sequence of PepD was conserved. That is, the deduced amino acid sequence thus obtained was the same as the amino acid sequence indicated by SEQ NO. 3. In the specimens of the patient strains A and B, the deduced amino acid sequence had one mutation of amino acid. Specifically, an amino acid residue positioned $11^{th}$ from N-terminus of the amino acid sequence indicated by SEQ NO. 3 was changed from Gln to Lys. This mutation was also observed in strains derived from Riken BioResource Center which were used to determine the anti-inflammatory effect of individual peptides in the Examples. The patient strain A is a specimen derived from the acne patient in the Example 6.

TABLE 4

| specimen | PCR | | Amino acid sequence | |
|---|---|---|---|---|
| | PepA | PepD | PepA | PepD |
| strain derived from Riken (JCM6425) | positive | positive | Sequence conservation | Partial mutation ($^{11}$Gln→Lys) |
| Patient strain A | positive | positive | Sequence conservation | Partial mutation ($^{11}$Gln→Lys) |
| Patient strain B | positive | positive | Sequence conservation | Partial mutation ($^{11}$Gln→Lys) |
| Patient strain C | positive | positive | Sequence conservation | Sequence conservation |
| Patient strain D | positive | negative | Sequence conservation | — |
| Patient strain E | positive | positive | Sequence conservation | Sequence conservation |

However, as shown in the Example 5 and FIG. 5, single administration of PepD can yield an anti-inflammatory effect on inflammation caused by strains derived from RIKEN BioResource Center which contain mutation in the amino acid sequence of PepD. This shows that PepD can serve as a vaccine effectively even on inflammation caused by strains containing PepD having mutation of one amino acid.

Similarly, in *P. acnes* in the specimens collected from the 30 volunteers shown in Table 5, DNA encoding the amino acid sequence of PepA and DNA encoding the amino acid sequence of PepD were amplified by PCR and base sequences of respective PCR products were determined, so that respective deduced amino acid sequences were determined. Table 5 shows the results.

TABLE 5

| PCR detection (simple) | Number of cases | Number of cases of complete sequence conservation | Number of cases of partial sequence mutation | Number of cases of unidentified sequence |
|---|---|---|---|---|
| PepA positive | 30 | 30 | 0 | 0 |
| PepA negative | 0 | 0 | 0 | 0 |
| PepD positive | 26 | 20 | 6 ($^{11}$Gln→Lys in all cases) | 0 |
| PepD negative | 4 | 0 | 0 | 4 |

As shown in Table 5, in all the specimens examined here, the amino acid sequence of PepA was conserved completely. The results of Tables 4 and 5 show that the PepA sequence of actual patient-derived *P. acnes* was conserved very well.

On the other hand, in the 20 cases out of the 30 cases examined, the amino acid sequence of PepD was conserved completely (66.7%). In the 6 cases out of the cases examined, the amino acid sequence was partially mutated ($^{11}$Gln→Lys). This is a partial mutation equal to that of the RIKEN BioResource Center strains to which administration of a vaccine was found to be effective by the test using mice. Accordingly, in view of the effectiveness of a vaccine effect, the PepD sequence is supposed to be effective in 26 cases out of the 30 cases (86.7%). That is, the PepD sequence was conserved well.

In view of the above, it is considered that PepA and PepD have sequences which are well conserved in bacterial cells of patients, and therefore are highly effective as vaccines for patients.

Example 9

Vaccine Use Against *P. acnes*

[Preparation of Vaccine]

As described above, it was found in the acne inflammatory causing test system using mice in the Example 5 that two kinds of single chain peptides (PepA and PepD) have an anti-inflammatory effect. In order that these peptides work more effectively, MAP peptides for PepA and PepD were synthesized by the MAP process. The synthesis peptide thus obtained consisted of 7-13 molecules of the single chain peptide of PepA or PepD bound to a MAP structure. A MAP peptide mixture solution in which the MAP peptides for PepA and PepD, respectively, were mixed was prepared and used as a vaccine.

Preparation of the mixture solution was made as follows. Initially, individual MAP peptides were prepared, and then dialyzed with distilled water, and freeze-dried and powdered. Subsequently, respective powders were dissolved in physiological saline (produced by Otsuka Pharmaceutical Co., Ltd.) so that concentrations of the respective MAP peptides were 1 mg/ml (each of the resulting solutions are hereinafter referred to as "PA-MAP solution"). The PA-MAP solutions were subjected to an endotoxin examination and a cytotoxic examination. The amount of endotoxin met the allowable amount (5 EU or less/kg weight/1 shot) according to NIH. Further, in the cytotoxic examination, 10 µl of a test peptide solution and 90 µl of peripheral-blood mononuclear cells ($2 \times 10^6$ cells/ml in plain RPMI 1640) were co-cultured at 37° C. for 24 hours. The cell survival ratio was substantially equal (with difference of ±5% or less) to that of a control in which peripheral-blood mononuclear cells to which physiological saline was added were cultured, and consequently no toxicity was found.

[Case 1]

Figure 8:
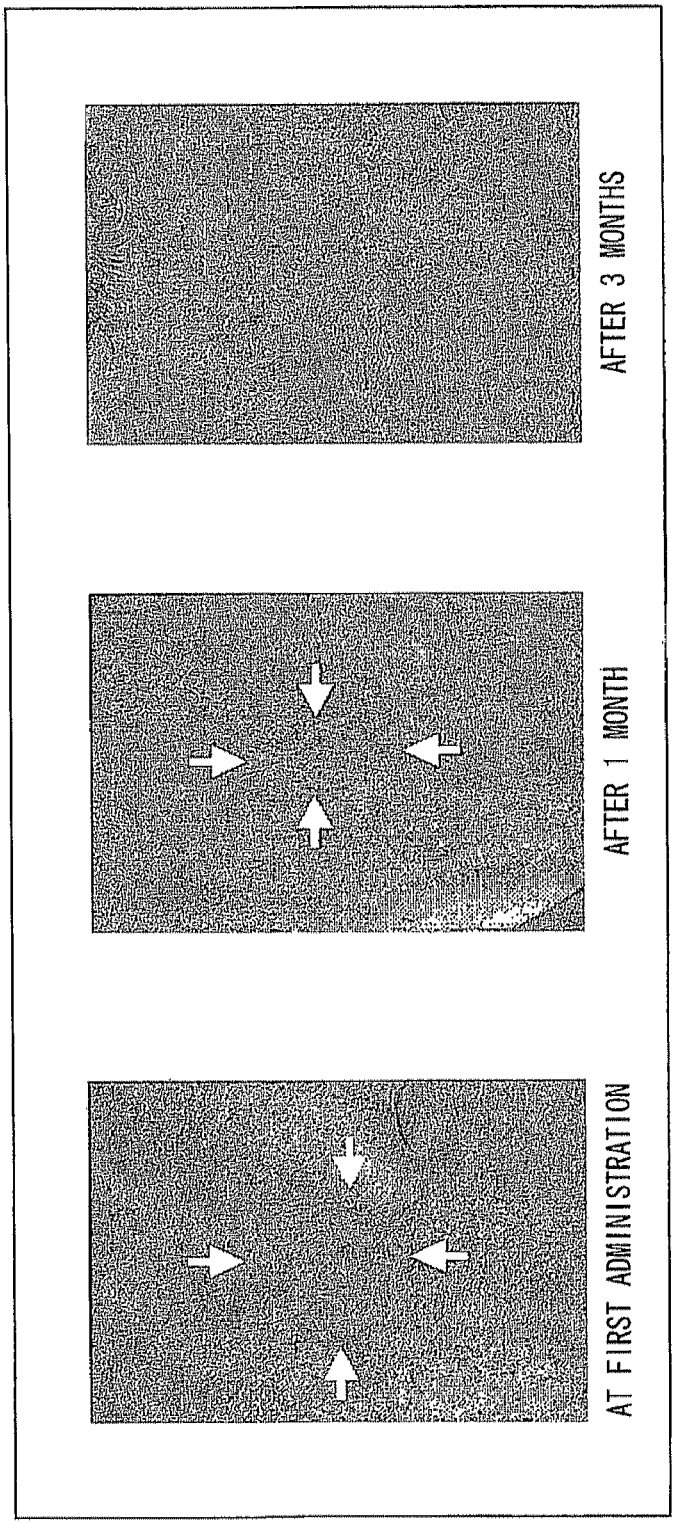
FIG. 8 is a diagram showing photos of follow-ups of an acne patient vaccinated with a vaccine of the present invention.

100 µl of the prepared PA-MAP solution was hypodermically vaccinated into an upper arm of the acne patient five times at an interval of 5 days. The acne patient was a patient carrying the patient strain A in the Example 8. FIG. 8 shows the result of observation.

As shown in FIG. 8, before the treatment (at first administration), whole areas of skin bulged and elevated (indicated by arrows in the drawing) due to hypodermic proliferation of acne bacterium, accompanied by inflammation. 1 month after the first vaccination, although bulge and elevation of acne were still observed, they were divided into two areas and inflammation was improved and localized. 3 months after the last vaccination, inflammation was decreasing gradually, acne was turning into scars, and the bulge and elevation were becoming flat. Since it was in the course of the treatment, pigmentary deposit was observed. There was observed no malign phenomenon caused by vaccination.

[Case 2]

A specimen was collected from the acne patient carrying the patient strain C in the Example 8, and it was confirmed whether the acne patient was infected with *P. acnes* or not by amplifying 16S rDNA of *P. acnes* by PCR. The result showed that the acne patient was *P. acnes* positive. Amplification of 16S rDNA of *P. acnes* was carried out using (i) primer L1 consisting of the same sequence as the primer 9F and (ii) primer R2: 5'-GCACGTAGTTAGCCGGTGCT-3' (SEQ NO. 13) by PCR consisted, of (i) a step at 95° C. for 5 min, and thereafter (ii) 35 cycles each consisting of a step at 95° C. for 15 sec, a step at 55° C. for 20 sec, and a step at 72° C. for 30 sec and (iii) a step at 72° C. for 7 min.

Figure 9:
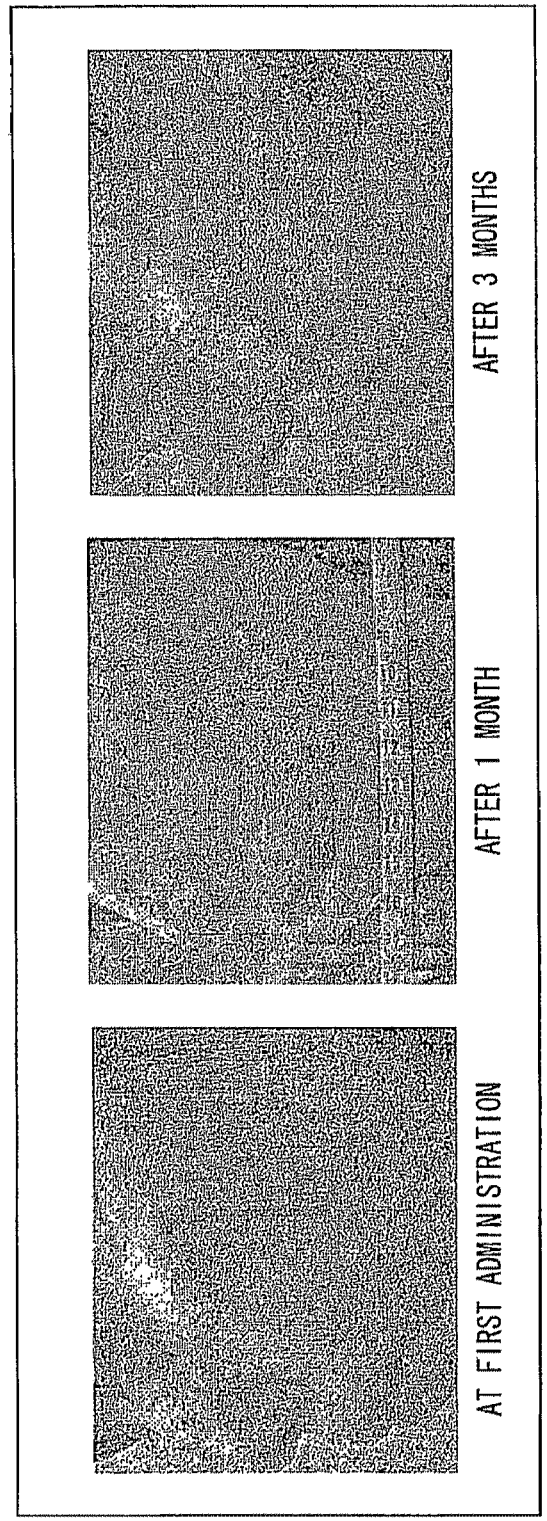
FIG. 9 is a diagram showing photos of follow-ups of another acne patient vaccinated with a vaccine of the present invention.

300 µl of the prepared PA-MAP solution was hypodermically vaccinated into an upper arm of the acne patient five times at an interval of 3 days. FIG. 9 shows the result of observation.

As shown in FIG. 9, whole areas of inflammation on the cheek observed before the treatment (at first administration) were improved 1 month and 3 month after the first vaccination. There was observed no malign phenomenon caused by vaccination.

[Case 3]

A specimen was collected from the acne patient carrying the patient strain D in the Example 8, and it was confirmed whether the acne patient was infected with *P. acnes* or not by amplifying 16S rDNA of *P. acnes* by PCR under the same conditions as those in the Case 2. The result showed that the acne patient was *P. acnes* positive.

Figure 10:
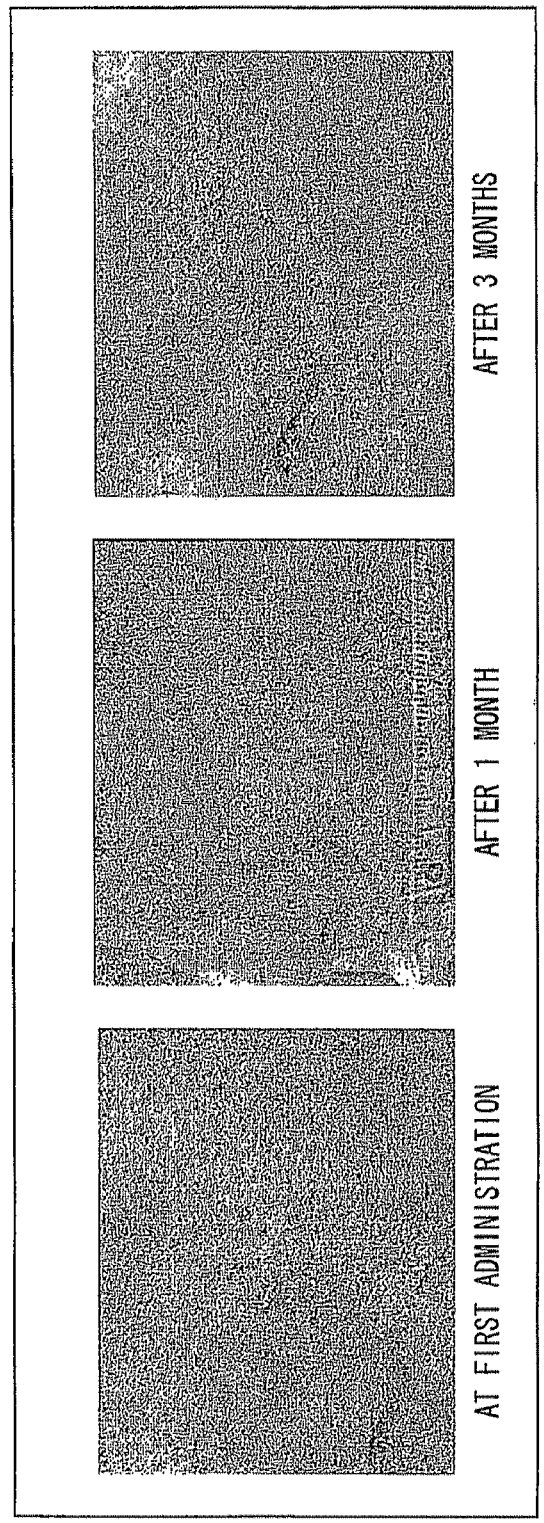
FIG. 10 is a diagram showing photos of follow-ups of still another acne patient vaccinated with a vaccine of the present invention.

300 µl of the prepared PA-MAP solution was hypodermically vaccinated into an upper arm of the acne patient five times at an interval of 3 days. FIG. 10 shows the result of observation.

As shown in FIG. 10, whole areas of inflammation around the nose observed before the treatment (at first administration) were improved 1 month and 3 month after the first vaccination. There was observed no malign phenomenon caused by vaccination.

[Case 4]

A specimen was collected from the acne patient carrying the patient strain E in the Example 8, and it was confirmed whether the acne patient was infected with *P. acnes* or not by amplifying 16S rDNA of *P. acnes* by PCR under the same conditions as those in the Case 2. The result showed that the acne patient was *P. acnes* positive.

Figure 11:
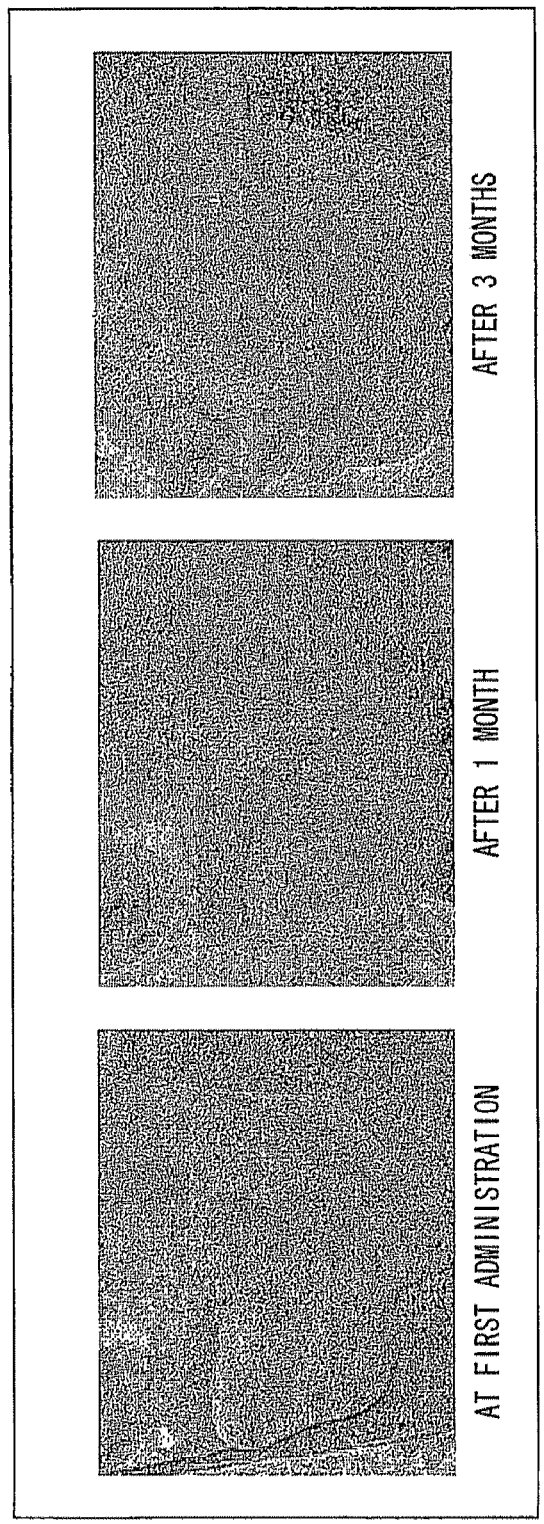
FIG. 11 is a diagram showing photos of follow-ups of yet another acne patient vaccinated with a vaccine of the present invention.

300 µl of the prepared PA-MAP solution was hypodermically vaccinated into an upper arm of the acne patient five times at an interval of 5 days. FIG. 11 shows the result of observation.

As shown in FIG. 11, whole areas of inflammation on wide areas of the cheek observed before the treatment (at first administration) were improved 1 month and 3 month after the first vaccination. There was observed no malign phenomenon caused by vaccination.

The above results show that the composition containing the peptide PepA and the peptide PepD is effective as a vaccine against *P. acnes*, i.e. an acne vaccine.

INDUSTRIAL APPLICABILITY

Use of the present invention enables an immunotherapy for prevention and treatment of acne. Accordingly, the present invention is applicable to medical fields, pharmaceutical fields etc. and is very useful.

SEQUENCE LISTING

HK1005 Sequence Listing

The invention claimed is:

1. A peptide consisting of the amino acid sequence of SEQ NO. 1.

2. A fusion peptide, which is in a form of a multivalent antigen peptide comprising two or more of the peptide of claim 1 operably linked.

3. A pharmaceutical composition for reducing inflammation caused by *Propionibacterium acnes*, comprising the fusion peptide as set forth in claim 2 and a pharmaceutically acceptable carrier.

4. The pharmaceutical composition of claim 3, which is in the form of a solution, a suspension, a tablet, a pill, a capsule, a sustained release formulation or a powder.

5. The pharmaceutical composition of claim 3, further comprising an adjuvant.

6. The pharmaceutical composition of claim 5, wherein the adjuvant is selected from the group consisting of aluminum hydroxide, aluminum phosphate, aluminum potassium sulfate (alum), beryllium sulfate, silica, kaoline, carbon, water-in-oil type emulsion, oil-in-water type emulsion, Muramyl dipeptide, bacterial endotoxin, fat X, *Bordetella pertussis, Corynebacterium parvum*, polyribonucleotide, sodium alginate, lanoline, lysolecithin, vitamin A, sponin, liposome, levamisole, DEAE-dextran, block copolymer, and combinations thereof.

7. The fusion peptide of claim 2, wherein the two of more of the peptides are operably linked by a linker.

8. A composition, comprising:
the peptide as set forth in claim 1, or a fusion peptide which is in a form of a multivalent antigen peptide comprising two or more of the peptide of claim 1 operably linked.

9. A pharmaceutical composition for reducing inflammation caused by *Propionibacterium acnes*, comprising the peptide as set forth in claim 1 and a pharmaceutically acceptable carrier.

10. The pharmaceutical composition of claim 9, which is in the form of a solution, a suspension, a tablet, a pill, a capsule, a sustained release formulation or a powder.

11. The pharmaceutical composition of claim 9, further comprising an adjuvant.

12. The pharmaceutical composition of claim 11, wherein the adjuvant is selected from the group consisting of aluminum hydroxide, aluminum phosphate, aluminum potassium sulfate (alum), beryllium sulfate, silica, kaoline, carbon, water-in-oil type emulsion, oil-in-water type emulsion, Muramyl dipeptide, bacterial endotoxin, fat X, *Bordetella pertussis, Corynebacterium parvum*, polyribonucleotide, sodium alginate, lanoline, lysolecithin, vitamin A, sponin, liposome, levamisole, DEAE-dextran, block copolymer, and combinations thereof.

* * * * *

```
                        SEQUENCE LISTING

<160> NUMBER OF SEQ ID NOS: 16

<210> SEQ ID NO 1
<211> LENGTH: 14
<212> TYPE: PRT
<213> ORGANISM: Propionibacterium acnes

<400> SEQUENCE: 1

Ala Ile Gln Glu Lys Tyr Gly Asp Asp Arg Glu Arg Ala Gly
1               5                   10

<210> SEQ ID NO 2
<211> LENGTH: 42
<212> TYPE: DNA
<213> ORGANISM: Propionibacterium acnes

<400> SEQUENCE: 2
gccatccagg aaaagtacgg cgacgacagg gaacgtgccg gc                        42

<210> SEQ ID NO 3
<211> LENGTH: 13
<212> TYPE: PRT
<213> ORGANISM: Propionibacterium acnes

<400> SEQUENCE: 3

Lys Asp Ala Asp Lys Asp Asn Pro Thr Tyr Gln Lys Val
1               5                   10

<210> SEQ ID NO 4
<211> LENGTH: 39
<212> TYPE: DNA
<213> ORGANISM: Propionibacterium acnes

<400> SEQUENCE: 4
aaggacgctg acaaagacaa cccgacgtac cagaaggtc                            39

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtttgatcct ggctca                                                     16

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taccagggta tctaatcc                                                   18

<210> SEQ ID NO 7
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
gtattaccgc ggctgctgg                                                    19

<210> SEQ ID NO 8
<211> LENGTH: 511
<212> TYPE: DNA
<213> ORGANISM: Propionibacterium acnes

<400> SEQUENCE: 8
agagtttgat cctggctcag gacgaacgct ggcggcgtgc ttaacacatg caagtcgaac        60
ggaaaggccc tgcttttgtg gggtgctcga gtggcgaacg ggtgagtaac acgtgagtaa       120
cctgcccttg actttgggat aacttcagga aactgggggct aataccggat aggagctcct      180
gctgcatggt gggggttgga agtttcggc ggttggggat ggactcgcgg cttatcagct        240
tgttggtggg gtagtggctt accaaggctt tgacgggtag ccggcctgag agggtgaccg       300
gccacattgg gactgagata cggcccagac tcctacggga ggcagcagtg gggaatattg       360
cacaatgggc ggaagcctga tgcagcaacg ccgcgtgcgg gatgacggcc ttcgggttgt       420
aaaccgcttt cgcctgtgac gaagcgtgag tgacggtaat gggtaaagaa gcaccggcta      480
actacgtgcc agcagccgcg gtgatacgta g                                     511

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatgaaagcc atccaggaaa                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcacacgaaa caacgctaga                                                   20

<210> SEQ ID NO 11
<211> LENGTH: 17
<212> TYPE: PRT
<213> ORGANISM: Propionibacterium acnes

<400> SEQUENCE: 11

Gly Arg Lys Pro Asp Thr Asn Lys Arg Ser Trp His Arg Lys Ala Ser
1               5                   10                  15

Arg

<210> SEQ ID NO 12
<211> LENGTH: 22
<212> TYPE: PRT
<213> ORGANISM: Propionibacterium acnes
```

<400> SEQUENCE: 12

Ile Asp Gln Val Arg Glu Tyr Arg His Arg Asp Asp Asp Asp Glu
1               5                   10                  15

Asp Pro Gly Glu Asp Gly
            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcacgtagtt agccggtgct                                                    20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtgctgtcg tcaataacaa cttc                                               24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggagtggcca gagacgatct                                                    20

<210> SEQ ID NO 16
<211> LENGTH: 504
<212> TYPE: DNA
<213> ORGANISM: Propionibacterium acnes

<400> SEQUENCE: 16
gtttgatcct ggctcaggac gaacgctggc ggcgtgctta acacatgcaa gtcgaacgga        60
aaggccctgc ttttgtgggg tgctcgagtg gcgaacgggt gagtaacacg tgagtaacct       120
gcccttgact tgggataac ttcaggaaac tgggctaat accggatagg agctcctgct         180
gcatggtggg ggttggaaag tttcggcggt tggggatgga ctcgcggctt atcagcttgt       240 tggtgggta gtggcttacc aaggctttga cgggtagccg gcctgagagg gtgaccggcc        300
acattgggac tgagatacgg cccagactcc tacgggaggc agcagtgggg aatattgcac       360
aatgggcgga agcctgatgc agcaacgccg cgtgcgggat gacggccttc gggttgtaaa       420
ccgctttcgc ctgtgacgaa gcgtgagtga cggtaatggg taaagaagca ccggctaact       480
acgtgccagc agccgcggtg atac                                              504